(12) United States Patent
Centanni

(10) Patent No.: US 7,431,886 B2
(45) Date of Patent: Oct. 7, 2008

(54) METHOD OF MONITORING OPERATIONAL STATUS OF SENSING DEVICES FOR DETERMINING THE CONCENTRATION OF CHEMICAL COMPONENTS IN A FLUID

(75) Inventor: Michael A Centanni, Parma, OH (US)

(73) Assignee: Steris Corporation, Mentor, OH (US)

( * ) Notice: Subject to any disclaimer, the term of this patent is extended or adjusted under 35 U.S.C. 154(b) by 841 days.

(21) Appl. No.: 10/949,930

(22) Filed: Sep. 24, 2004

(65) Prior Publication Data

US 2006/0073077 A1   Apr. 6, 2006

(51) Int. Cl.
*G01N 27/00* (2006.01)

(52) U.S. Cl. .................................. 422/82.01
(58) Field of Classification Search ............... 422/82.01
See application file for complete search history.

(56) References Cited

U.S. PATENT DOCUMENTS

| | | | |
|---|---|---|---|
| 3,164,004 A | 1/1965 | King, Jr. | |
| 3,327,519 A | 6/1967 | Crawford | |
| 3,464,797 A | 9/1969 | Hagopain | 23/232 |
| 3,636,444 A | 1/1972 | Strawn et al. | 324/61 R |
| 3,778,706 A | 12/1973 | Thompson | 324/61 R |
| 3,816,811 A | 6/1974 | Cmelik | 324/61 R |
| 4,031,742 A | 6/1977 | Michael et al. | 73/40.7 |
| 4,111,036 A | 9/1978 | Frechette et al. | 73/24.06 |
| 4,158,810 A | 6/1979 | Leskovar | 324/127 |
| 4,163,384 A | 8/1979 | Blakemore | 73/29 |
| 4,219,776 A | 8/1980 | Arulanandan | 324/323 |
| 4,236,893 A | 12/1980 | Rice | 23/230 B |
| 4,242,096 A | 12/1980 | Oliveira et al. | 23/230 B |
| 4,314,821 A | 2/1982 | Rice | 23/230 B |
| 4,427,772 A | 1/1984 | Kodera et al. | 435/27 |
| 4,509,522 A | 4/1985 | Manuccia et al. | 128/634 |
| 4,525,265 A | 6/1985 | Abe et al. | 204/403 |
| 4,674,879 A | 6/1987 | Gregorig et al. | 356/301 |
| 4,788,466 A | 11/1988 | Paul et al. | 310/316 |
| 4,849,178 A | 7/1989 | Azuma | 422/69 |
| 4,857,152 A | 8/1989 | Armstrong et al. | 204/1 T |
| 5,151,660 A | 9/1992 | Powers et al. | 324/689 |

(Continued)

FOREIGN PATENT DOCUMENTS

WO   WO 9857673 A1 * 12/1998

OTHER PUBLICATIONS

McDonnell, G.; Russel, A. D. "Antiseptics and Disinfectants: Activity, Action, and Resistance." Clinical Microbiology Reviews. 1999, pp. 147-179.*

(Continued)

*Primary Examiner*—Walter D. Griffin
*Assistant Examiner*—Bobby Ramdhanie
(74) *Attorney, Agent, or Firm*—Kusner & Jaffe; Michael A. Centanni

(57) ABSTRACT

The present invention provides a sensor system for determining a concentration of a chemical component in a fluid having a first sensor that senses a first physico-chemical property of the chemical component and, a second sensor that senses a second, different physico-chemical property of the chemical component. A method to detect, control, monitor, maintain and confirm concentration levels of a decontaminant throughout a decontamination cycle is also provided.

15 Claims, 4 Drawing Sheets

U.S. PATENT DOCUMENTS

| | | | |
|---|---|---|---|
| 5,157,968 A | 10/1992 | Zfira | 73/149 |
| 5,171,523 A | 12/1992 | Williams | 422/20 |
| 5,243,858 A | 9/1993 | Erskine et al. | 73/204.26 |
| 5,339,675 A | 8/1994 | DiLeo et al. | 73/24.04 |
| 5,364,510 A | 11/1994 | Carpio | 204/153.1 |
| 5,439,569 A | 8/1995 | Carpio | 204/153.1 |
| 5,459,568 A | 10/1995 | Yano et al. | 356/336 |
| 5,470,754 A | 11/1995 | Rounbehler et al. | 436/106 |
| 5,595,908 A | 1/1997 | Fawcett et al. | 435/287.2 |
| 5,600,142 A | 2/1997 | Van Den Berg et al. | 250/339.13 |
| 5,700,375 A | 12/1997 | Hagen et al. | 210/651 |
| 5,756,631 A | 5/1998 | Grate | 528/26 |
| 5,847,276 A | 12/1998 | Mimken et al. | 73/453 |
| 5,852,229 A * | 12/1998 | Josse et al. | 73/24.06 |
| 5,856,198 A | 1/1999 | Joffe et al. | 436/100 |
| 5,866,798 A | 2/1999 | Schönfeld et al. | 73/24.06 |
| 5,882,590 A | 3/1999 | Stewart et al. | 422/28 |
| 5,958,787 A * | 9/1999 | Schonfeld et al. | 436/116 |
| 5,997,685 A | 12/1999 | Radhamohan et al. | 156/345 |
| 6,077,480 A | 6/2000 | Edwards et al. | 422/28 |
| 6,162,409 A | 12/2000 | Skelley et al. | 423/239.1 |
| 6,171,867 B1 | 1/2001 | Feucht et al. | 436/124 |
| 6,196,052 B1 | 3/2001 | May et al. | 73/24.06 |
| 6,369,387 B1 | 4/2002 | Eckles | 250/343 |
| 6,410,332 B1 | 6/2002 | Desrosiers et al. | 436/37 |
| 6,454,874 B1 | 9/2002 | Jacobs et al. | 134/18 |
| 6,560,551 B1 | 5/2003 | Severson et al. | 702/54 |
| 6,614,242 B2 | 9/2003 | Matter et al. | 324/698 |
| 6,630,560 B2 | 10/2003 | McGill et al. | 528/25 |
| 6,660,231 B2 | 12/2003 | Moseley | 422/98 |
| 6,706,648 B2 | 3/2004 | Yamazaki et al. | 438/790 |
| 2002/0014410 A1 | 2/2002 | Silveri et al. | 204/412 |
| 2002/0033186 A1 | 3/2002 | Verhaverbeke et al. | 134/26 |
| 2002/0076492 A1 | 6/2002 | Loan et al. | 427/255.28 |
| 2002/0109511 A1 | 8/2002 | Frank | 324/663 |
| 2002/0111040 A1 | 8/2002 | Yamazaki et al. | 438/783 |
| 2002/0157686 A1 | 10/2002 | Kenny et al. | 134/1.3 |
| 2003/0063997 A1 | 4/2003 | Fryer et al. | 422/3 |
| 2003/0102007 A1 | 6/2003 | Kaiser | 134/1 |
| 2003/0157587 A1 | 8/2003 | Gomez et al. | 435/30 |
| 2004/0029257 A1 | 2/2004 | Dutil et al. | 435/266 |
| 2004/0079395 A1 | 4/2004 | Kim et al. | 134/30 |
| 2004/0178799 A1 | 9/2004 | Korenev et al. | 324/453 |
| 2004/0178802 A1 | 9/2004 | Centanni | 324/662 |
| 2004/0178803 A1 | 9/2004 | Centanni | 324/662 |
| 2004/0178804 A1 | 9/2004 | Allen et al. | 324/662 |
| 2004/0249579 A1 | 12/2004 | Centanni | 702/25 |
| 2004/0262170 A1 | 12/2004 | Centanni | 205/782 |

OTHER PUBLICATIONS

Ishihara, Tatsumi et al. "Mixed oxide capacitor of barium titanate-lead oxide as a new type of carbon dioxide gas sensor," Chemistry Letters (1990), (7), pp. 1163-1166.

Steven J. Lasky, Howard R. Meyer & Daniel A. Buttry, Department of Chemistry, "Quartz Microbalance Studies of Solvent and Ion Transport in Thin Polymer Films in Sensor Applications of the QCH," *Technical Digest* 1990, pp. 1-4.

Sylvain Lazare and Vincent Granier, "Excimer Laser Light Induced Ablation and Reactions at Polymer Surfaces as Measured with a Quartz-Crystal Microbalance," Nov. 16, 1987, J. Appl. Phys 63 (6), Mar. 15, 1988, 1988 *American Institute of Physics*, pp. 2110-2115.

Stanley Bruckenstein, C. Paul Wilde, Michael Shay and A. Robert Hillman, "Experimental Observations on Transport Phenomena Accompanying Redox Switching in Polythionine Films Immersed in Strong Acid Solutions," 1990 American Chemical Society, pp. 787-793.

Robert R. McCaffrey, Stanley Bruckenstein and Paras N. Prasad, "Novel Application of the Quartz Crystal Microbalance to Study Langmuir-Blodgett Films," 1986 *American Chemical Society*, pp. 228-229.

J.A. Moore and Sang Youl Kim, "Diffusion of Small Molecules in Radiation Damaged PMMA Thin Films," 2002 Engineering Info. Inc., pp. 383-386.

Rade Ognjanovic, C.-Y. Hui, E.J. Kramer, "The Study of Polystyrene Surface Swelling by Quartz Crystal Microbalance and Rutherford Backscattering Techniques," *Journal of Materials Science* 25 (1990), 1990 Chapman and Hall Ltd., pp. 514-518.

H.G. Tompkins, "Use of Surface and Thin Film Analysis Techniques to Study Metal-Organic and Metal-Polymer Interaction: A Review," *Thin Solid Films*, 119 (1984), pp. 337-348.

Sylvain Lazare, Jean Claude Soulignac and Pascal Fragnaud, "Direct and Accurate Measurement of Etch Rate of Polymer Films under Far-UV Irradiation," Appl. Phys. Lett. 50 (10), Mar. 9, 1987, 1987 American Institute of Physics, pp. 624-625.

Aljosa Vrhunec, Andreja Kolenc, Dusan Teslic, Iztok Livk and Ciril Pohar, "Crystal Size Distribution in Batch Sodium Perborate Precipitation," *Acta Chim. Slov.* 1999, 46(4), pp. 543-554.

Philipp, "Charge Transfer Sensing," 1997.

Wojslaw, "Everything You Wanted to Know About Digitally Programmable Potentiometers," Catalyst Semiconductor, Inc., Oct. 17, 2001, Publication No. 6009.

Kittel, "Introduction to Solid State Physics," Fourth Edition, John Wiley & Sons, Inc., 1971.

Philipp, "The Charge Transfer Sensor," Sensors Magazine, Oct. 1999.

T. J. Buckley et al., "Toroidal Cross Capacitor for Measuring the Dielectric Constant of Gases," Review of Scientific Instruments, vol. 71, No. 7, Jul. 2000, pp. 2914-2921.

Gross et al., "The Dielectric Constants of Water Hydrogen Peroxide and Hydrogen Peroxide-Water Mixtures," L. Amer. Chem. Soc., vol. 72, 1950, pp. 2075-2080.

"Humidity Sensor Theory and Behavior," Psychometrics and Moisture, Honeywell HVAC, Nov. 27, 2002.

U.S. Appl. No. 10/456,380, filed Jun. 6, 2003, Centanni, entitled: Method and Apparatus for Formulating and Controlling Chemical Concentrations in a Gas Mixture.

U.S. Appl. No. 10/872,227, filed Jun. 18, 2004, Kaiser et al., entitled: Method and Apparatus for Monitoring the Purity and/or Quality of Steam.

U.S. Appl. No. 10/896,609, filed Jul. 21, 2004, Kaiser et al., entitled: Method and Apparatus for Real Time Monitoring of Metallic Cation Concentrations in a Solution.

U.S. Appl. No. 10/900,745, filed Jul. 28, 2004, Kaiser et al., entitled: Method and Apparatus for Monitoring the State of a Chemical Solution for Decontamination of Chemical and Biological Warfare Agents.

U.S. Appl. No. 10/931,186, filed Aug. 31, 2004, Kaiser et al., entitled: Method and Apparatus for Monitoring Detergent Concentration in a Decontamination Process.

U.S. Appl. No. 10/987,072, filed Nov. 12, 2004, Centanni, entitled, Sensor for Determining Concentration of Ozone.

U.S. Appl. No. 10/663,593, filed Sep. 16, 2003, Centanni et al., entitled: Sensor for Determining Concentration of Fluid Sterilant.

\* cited by examiner

METHOD OF MONITORING OPERATIONAL STATUS OF SENSING DEVICES FOR DETERMINING THE CONCENTRATION OF CHEMICAL COMPONENTS IN A FLUID

FIELD OF INVENTION

The present invention generally relates to the determination of chemical concentrations, and more particularly, to a method and apparatus for determining the concentration of a chemical component in a liquid or gaseous system using multiple sensors.

BACKGROUND OF INVENTION

Where appropriate, electronic sensing devices are used to detect, monitor, measure and control the concentrations of various chemical components in chemical feed streams and in chemical operations. One such chemical operation in which electronic sensing devices find utility is in the decontamination of medical instruments. In decontamination systems, it is advantageous to maintain the concentration of a decontaminant, i.e., the decontaminating agent, at a specified concentration for a certain period of time, thus optimizing the decontamination process. Generally, "decontaminating" refers to all levels of inactivating biocontamination, including, but not limited to, the process of sanitizing, disinfecting or sterilizing. A decontamination processes may involve liquid, vaporous or gaseous processes. It should be understood that the term "decontamination," as used herein, also refers to washing with a detergent or other cleaning agent. Examples of apparatus that decontaminate by washing include, by way of example and not limitation, washing machines of all types including domestic and industrial dishwashing machines, domestic and industrial clothes washing machines and industrial washers such as those used to wash and clean soiled medical instruments. In addition, as used herein, decontamination also refers to the process of neutralizing bio-warfare and/or chemical warfare agents.

Given the importance of maintaining a specific decontaminant concentration level when treating medical instruments or other articles, it would be advantageous to have a sensing apparatus that is capable of maintaining and confirming the concentration levels of specific decontaminants during a decontamination process.

The present invention describes a method and an apparatus that detects, controls, monitors, maintains and confirms the concentration of a chemical in a chemical process.

SUMMARY OF THE INVENTION

In accordance with a preferred embodiment of the present invention, there is provided a system for use in determining a concentration of a chemical component in a fluid, comprising: (a) a processing system; (b) a first sensor that communicates to the processing system, the first sensor responsive to a first physico-chemical property of the chemical component; and (c) a second sensor that communicates to the processing system, the second sensor responsive to a second physico-chemical property of the chemical component.

In accordance with another aspect of the present invention, there is provided a system for use in determining a concentration of a decontaminant in a fluid, comprising: (a) a processing system; (b) a capacitor that communicates to the processing system, the capacitor responsive to a first physico-chemical property of the chemical component; and (c) a quartz crystal that communicates with the processing system, the quartz crystal supporting a chemical that interacts with the decontaminant, the quartz crystal responsive to a second physico-chemical property of the chemical component.

In accordance with yet another aspect of the present invention, there is provided a method of determining a concentration of a chemical component in a fluid, comprising the steps of: (a) sensing a first physico-chemical property of the chemical component by measuring a first electrical signal produced by a first sensor; (b) determining a first concentration of the chemical component by referencing the first electrical signal to a first set of stored data; (c) sensing a second, a second physico-chemical property of the chemical component by measuring a second electrical signal produced by a second sensor; (d) determining a second concentration of the chemical component by referencing the second electrical signal to a second set of stored data; and, (e) comparing the first concentration to the second concentration to determine whether the first concentration falls within a pre-set percentage of the second concentration.

An advantage of the present invention is the provision of a system that senses concentrations of decontaminants and is self-policing.

Another advantage of the present invention is the provision of a system that can provide historical data that a concentration of a decontaminant remained above a threshold value during the course of a decontamination process.

Another advantage of the present invention is the provision of a system that can alert an operator or abort a decontamination process in the event that a component of a chemical concentration sensor system is faulty.

Still another advantage of the present invention is the provision of a chemical concentration sensor system that can be easily replaced in the event that a component of the sensor system is faulty.

Still another advantage of the present invention is the provision of a system that can detect, measure, monitor and control the concentration of a variety of decontaminants such as: peracidic acid, liquid hydrogen peroxide, vaporized hydrogen peroxide, ozone, ethylene oxide and detergents.

Still another advantage of the present system is the provision of a chemical concentration sensor system that is reusable.

Yet another advantage of the present invention is the provision of an inexpensive chemical concentration sensor system.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
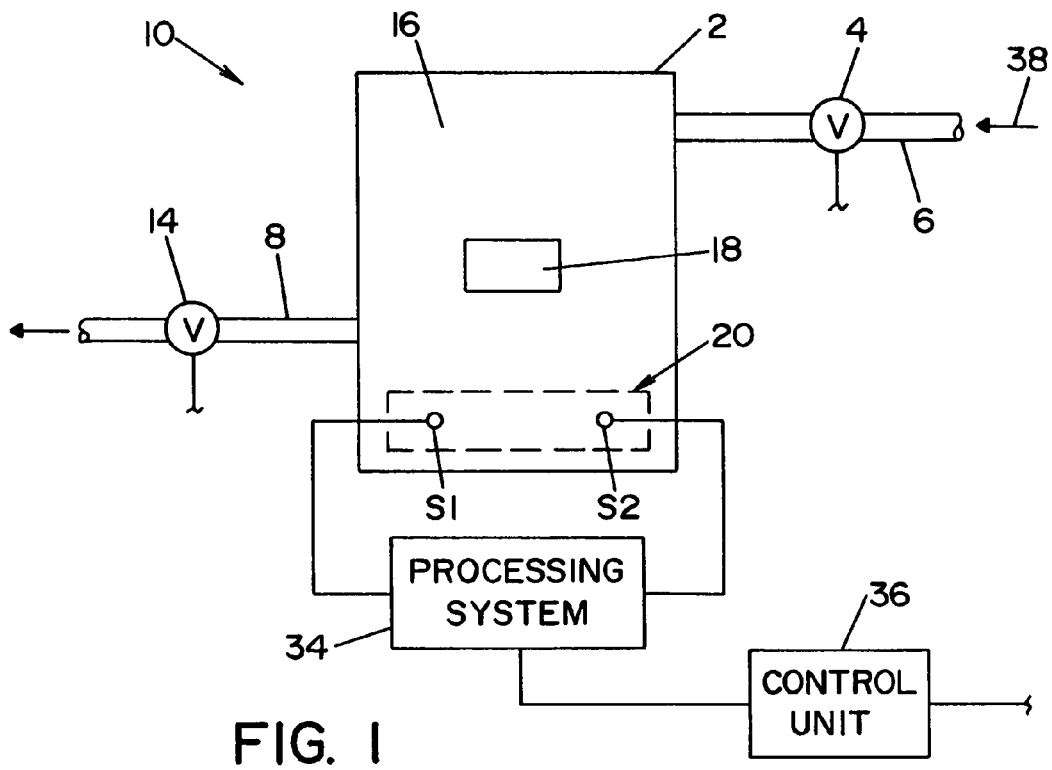
FIG. 1 is a schematic view of an exemplary decontamination system.

Referring now to the drawings wherein the showings are for the purposes of illustrating a preferred embodiment of the invention only and not for purposes of limiting the same, FIG. 1 shows a sterilization apparatus 10 according to an embodiment of the present invention. Sensor system 20 is generally comprised of two sensors, sensor S1 and sensor S2. Sensors S1 and S2 are both electrically connected to a processing system 34. In addition, sensor S1 or sensor S2 may communicate electromagnetically such as, by way of example, by radio waves, to processing system 34. Processing system 34 is preferably electrically connected with a control unit 36 that serves as a main control unit for sterilization system 10. Processing system 34 and/or control unit 36 may be electrically or electromagnetically connected with an output device (not shown), such as a speaker, a monitor, a display device and a printer, for providing audible and/or visual information.

Each of sensor S1 and sensor S2 of sensor system 20 with processing system 34, measures the concentration of a chemical component of a fluid introduced into a chamber as will described hereinbelow. Processing system 34 preferably takes the form of a microcomputer, microcontroller or microprocessor, and includes an internal or external data storage device, such as a RAM, a ROM, a hard drive, an optical data storage device, or other memory device.

By way of example, the preferred embodiment will be described in terms of a sterilization process. The invention, however, is not to be limited to use in a sterilization process.

Referring to FIG. 1, a fluid 38, the fluid being a liquid, gas, vapor or a combination of any of the foregoing, that contains a decontaminant that is to be detected, measured, monitored and controlled, enters a chamber 2 through an input line 6. The fluid may consist of, by way of example and not limitation, water, air, a decontaminant or a mixture thereof. Chamber 2, i.e., in the event fluid 38 is a gas and/or a vapor, may be a closed chamber, an open chamber, an isolator, a room or a building. In the event fluid 38 is a liquid, chamber 2 may be a container as found in conventional liquid sterilization systems, such as SYSTEM 1, marketed by the STERIS Corporation, Mentor, Ohio.

Valve 4 controls the rate at which fluid 38 enters chamber 2. Other means of controlling the rate at which fluid 38 enters chamber 2 are also contemplated. For example, in a vapor decontamination process, such as one that uses vaporized hydrogen peroxide, one could simply control the amount of vaporized hydrogen peroxide introduced into a carrier gas stream while keeping the flow rate of the carrier gas stream constant. Fluid 38 resides in an interior region 16 of chamber 2 and contacts medical instrument 18 to be decontaminated. In the event the decontamination process is a continuous process, fluid 38 is removed from chamber 2 by output line 8. Valve 14 controls the flow of fluid 38 through output line 8.

Still referring to FIG. 1, sensor system 20 will be described in further detail. As indicated above, sensor system 20 is comprised of at least two sensors shown as sensor S1 and sensor S2. Both sensors are electrically connected to a processing system 34.

In one embodiment, sensor S1 includes a capacitor that senses a change in the electrical properties of fluid 38 as the concentration of the decontaminant within fluid 38 fluctuates. Fluid 38 forms a dielectric between the electrical conductors of the capacitor, the electrical conductors forming the plates of the capacitor. Many fluids, such as, but not limited to, water, steam, hydrogen peroxide, vaporized hydrogen peroxide and ozone, have permanent electrical dipole moments. It is the presence, or in some cases, the absence, of electrical dipole moments in between the plates of the capacitor that is detected by capacitive sensor S1. It is thus believed that changes in the dielectric properties of fluid 38, i.e., as the concentration of the decontaminant changes, are reflected by changes in the electrical outputs of sensor S1. Changes in the electrical properties of fluid 38 are sensed by sensor S1 and are compared with data or graphs stored in the data storage device of processing system 34 that provide a correlation between changes in the electrical outputs of sensor S1 and the concentrations of the decontaminant present in fluid 38 that is being detected and monitored. Such a capacitive sensor is more fully described in U.S. patent application entitled, Method and Apparatus for Measuring Concentration of a Chemical Component in a Gas Mixture (Ser. No. 10/405,880) and U.S. patent application entitled, Method and Apparatus for Measuring Chemical Concentration In a Fluid (Ser. No. 10/389,036), which are both fully incorporated herein by reference.

Figure 3:
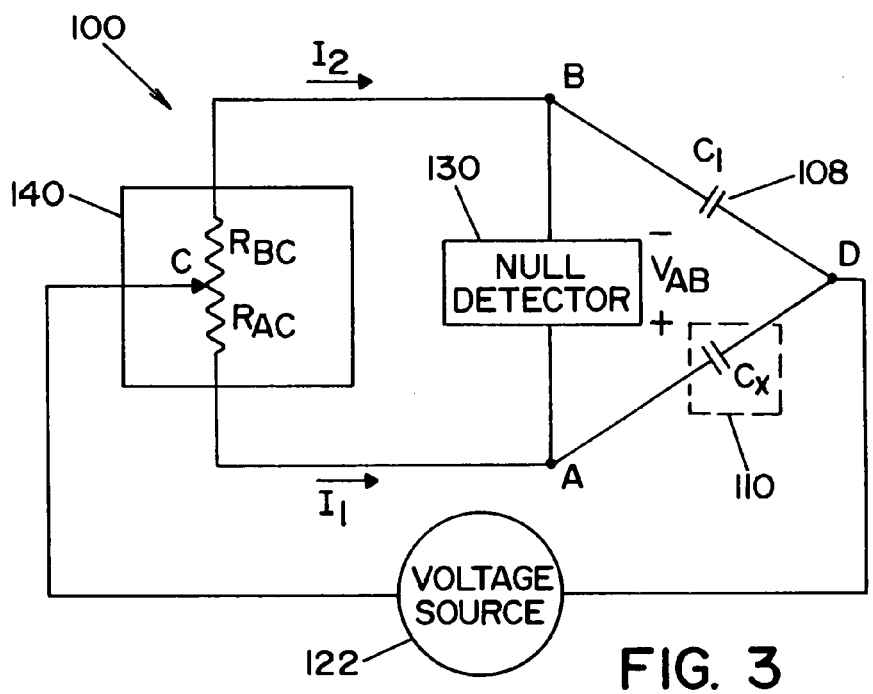
FIG. 3 is a schematic diagram of an exemplary capacitive sensor for determining the concentration of a chemical component, according to a first embodiment.

Referring now to FIG. 3, there is shown a block diagram of an exemplary sensor 100, according to a first embodiment, that may be used as sensor S1. Sensor 100 senses the concentration of chemical components by use of a capacitor. In the embodiment shown in FIG. 3, sensor 100 takes the form of a "bridge circuit." As is well known to those skilled in the art, bridge circuits are used to determine the value of an unknown impedance in terms of other impedances of known value. The bridge circuit is used to determine a capacitance value indicative of the concentration of chemical components in a fluid.

Sensor 100 is generally comprised of a voltage source 122 that acts as a signal generator, a null detector 130, an electronic potentiometer 140, a capacitor 108 of known capacitance $C_1$, and a capacitor 110 of capacitance $C_x$. Sensor 100 is electrically connected to processing system 34 to communicate electrical signals therebetween.

Capacitor 110 acts as a sensing element, and is directly exposed to the fluid in interior region 16 of chamber 2. The fluid fills the gap between the electrical conductors of capacitor 110, thereby acting as the insulator or "dielectric" of capacitor 110. In one embodiment, capacitor 110 is a parallel plate capacitor. However, it should be appreciated that capacitor 110 could be constructed in a different form, including, but not limited to, a cylindrical or spherical capacitor.

As indicated above, the output of sensor 100 will respond to changes in the concentration of chemical components in fluid 38. For example, capacitance $C_x$ will vary as the concentration of the chemical components in fluid 38 changes.

Figure 2:
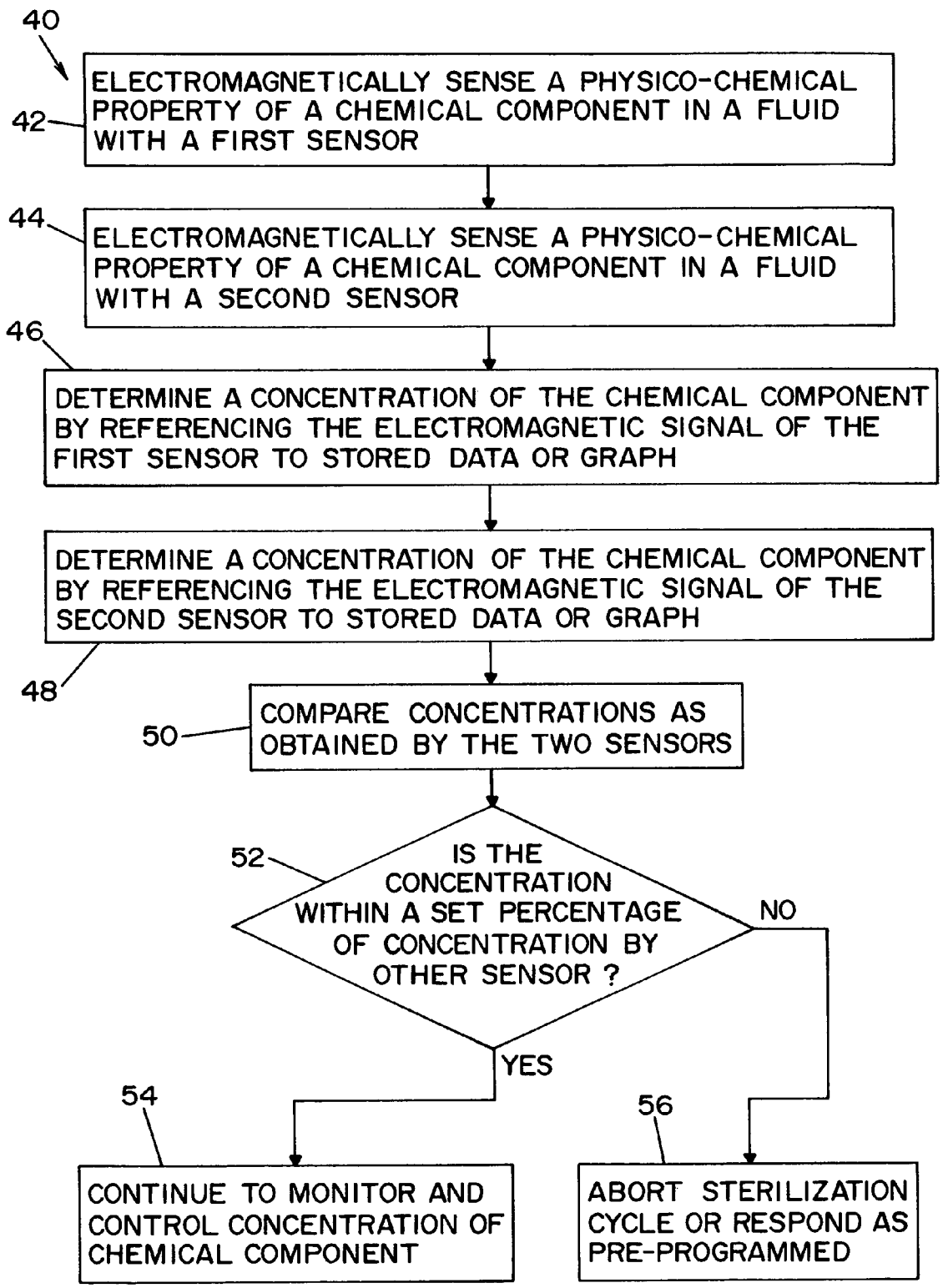
FIG. 2 is a flow diagram illustrating a preferred method of the present invention.

Referring now to FIG. 2, electronic potentiometer 140 functions in the same manner as a mechanical potentiometer. In this regard, electronic potentiometer 140 is a three terminal device. Between two of the terminals is a resistive element. The third terminal, known as the "wiper," is connected to various points along the resistive element. In a preferred embodiment, the wiper is digitally controlled by processing system 34 (see FIG. 1). The wiper divides the resistive element into two resistors $R_{BC}$ and $R_{AC}$. Electronic potentiometer 140 may take the form of a digitally programmable potentiometer (DPP™) available from Catalyst Semiconductor, Inc. of Sunnyvale, Calif.

Voltage source 122 provides an AC voltage signal, such as a sinusoidal or pulse waveform. Null detector 130 is a device for detecting a null condition (i.e., a short circuit), such as a galvanometer, a voltmeter, a frequency-selective amplifier, and the like.

Operation of sensor 100, as shown in FIG. 3, will now be described in detail. The elements of the bridge circuit are connected between junctions AC, BC, AD, and BD. Electronic potentiometer 140 is operated by processing system 34 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches: $V_{AC}=V_{BC}$, and $V_{AD}=V_{BD}$, where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $V_{AD}=V_{BD}/(V_{AC}/V_{BC})$.

Capacitor 110, having capacitance $C_x$, is connected between junctions A and D, and capacitor 108, having capacitance $C_1$, is connected between junctions B and D. Electronic potentiometer 140, connected from junction A to junction C to junction B, is adjusted by processing system 34 to vary the voltages $V_{AC}$ and $V_{BC}$.

When a null is detected by null detector 130, current $I_1$, flows from junction C to junction A to junction D, and a current $I_2$ flows from junction C to junction B to junction D. The voltage $V_{AC}$ across junctions A to C, and the voltage $V_{BC}$ across junctions B to C are: $V_{AC}=I_1 R_{AC}$ and $V_{BC}=I_2 R_{BC}$.

The voltage across a capacitor with capacitance C, current I, and frequency is:

$$V = \frac{I}{2\pi f C}$$

Therefore, the voltages $V_{AD}$ and $V_{BD}$ may be respectively expressed as:

$$V_{AD} = \frac{I_1}{2\pi f C_x} \text{ and } V_{BD} = \frac{I_2}{2\pi f C_1}$$

As discussed above, $V_{AD}=V_{BD}/(V_{AC}/V_{BC})$, $V_{AC}=I_1 R_{AC}$, and $V_{BC}=I_2 R_{BC}$. Therefore, $$C_x = C_1 \left(\frac{R_{BC}}{R_{AC}}\right).$$

In view of the foregoing relationship, when a null condition is detected, the resistance values for $R_{BC}$ and $R_{AC}$, along with the known capacitance value $C_1$, of capacitor 108, can be used to determine unknown value of capacitance $C_x$ of capacitor 110.

Sensor 100 utilizes differences in dipole moments of different molecules to determine the concentration of chemical components in a fluid. By configuring capacitor 110 as an element of a bridge circuit, a measure of resistance values $R_{AC}$ and $R_{BC}$, when the bridge is balanced or nulled, can be used to determine capacitance $C_x$ of capacitor 110. Capacitance $C_x$ is indicative of the concentrations of chemical components in the fluid.

Figure 4:
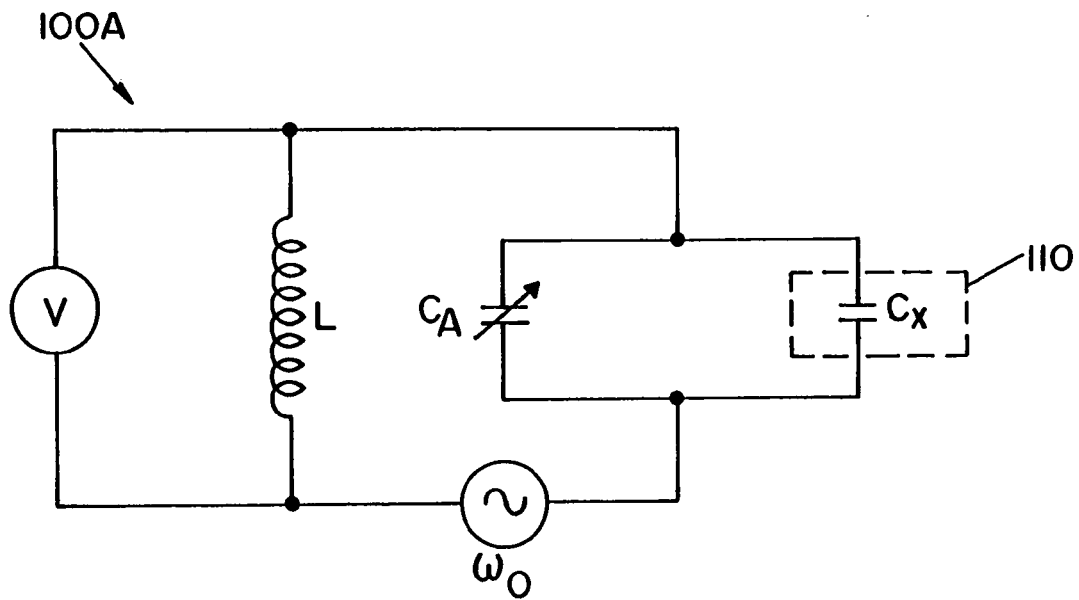
FIG. 4 is a schematic diagram of an exemplary capacitive sensor for determining the concentration of a chemical component, according to a second embodiment.

It should be appreciated that while the illustrated embodiment of sensor 100 takes the form of a bridge circuit, other types of circuits and techniques (including other types of bridge circuits, and capacitance meters) known to those skilled in the art, may be suitably used to measure capacitance. For example, FIG. 4 illustrates an alternative sensor 100A. Sensor 100A is an LC resonant circuit, having a variable capacitor $C_A$ and a capacitor 110 having a capacitance $C_x$ directly exposed to fluid 38 in interior region 16. Fluid 38 fills the gap between the electrical conductors of capacitor 110, thereby acting as the insulator or "dielectric" of capacitor 110. Since the resonance frequency $\omega_0=[L(C_A+C_x)]^{-1/2}$, the unknown capacitance of capacitor 110 can be determined.

Figure 5:
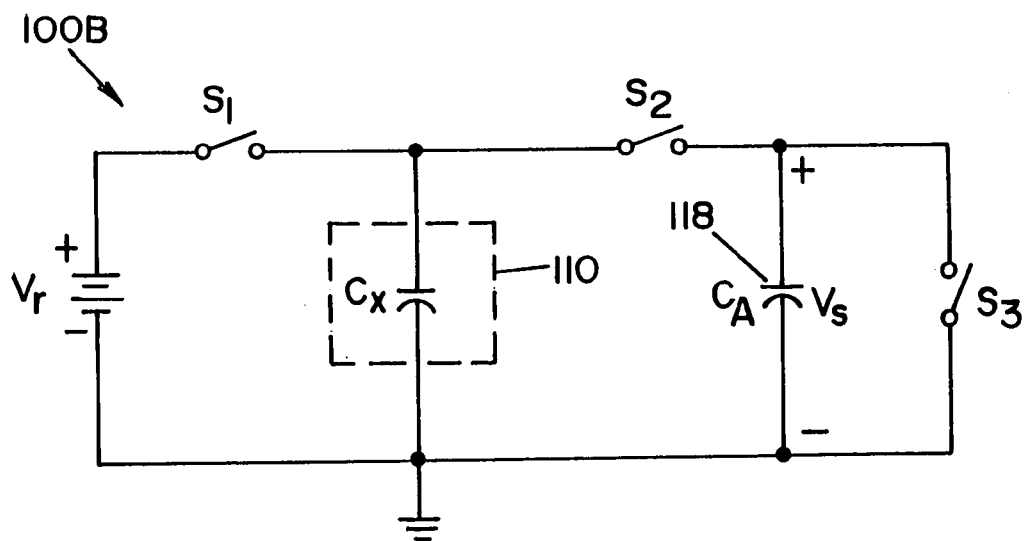
FIG. 5 is a schematic diagram of an exemplary capacitive sensor for determining the concentration of a chemical component, according to a third embodiment.

FIG. 5 illustrates yet another alternative liquid concentration sensor 100B suitable for use in connection with the present invention. In this embodiment, liquid concentration sensor 100B is a "charge transfer" sensor circuit. Charge transfer sensor circuits are recognized to provide resolutions of fractions of a femtoFarad. In a charge transfer sensor circuit the unknown capacitance $C_x$ of capacitor 110 is determined by charging the sense electrode to a fixed potential, and then transferring that charge to a charge detector comprising a capacitor 118 of known capacitance $C_A$. Fluid 38 inside interior region 16 fills the gap between the electrical conductors of capacitor 110, thereby acting as an insulator or "dielectric" of capacitor 110. Capacitor 110 is first connected to a DC reference voltage ($V_r$) via a switch $S_1$. Switch $S_1$ is reopened after capacitor 110 is satisfactorily charged to the potential of $V_r$. Then, after as brief as possible a delay so as to minimize leakage effects caused by conductance, switch $S_2$ is closed and the charge (Q) present on capacitor 110 is transferred to capacitor 118 (i.e., the charge detector). Once the charge Q is satisfactorily transferred to capacitor 118, switch $S_2$ is reopened. By reading voltage $V_s$, the capacitance $C_x$ of capacitor 110 can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Preferably, digital control logic is used to control switches $S_1$, $S_2$ and $S_3$. In a preferred embodiment, capacitor 118 is selected to have significantly more capacitance than capacitor 110. The equations governing this alternative embodiment are as follows:

$$V_s = V_r[C_x/(C_x+C_A)], \text{ therefore } C_x = V_s C_A/[V_r - V_s].$$

It is recognized that in some cases, the capacitance of the capacitor exposed to fluid 38 may be in the range of femtoFarad capacitance to low picoFarad capacitance (e.g., 1 fF to 100 pF), and that changes in concentration of a chemical component in fluid 38 may only result in a change of capacitance in the range of low picoFarad capacitance or even femtoFarad capacitances. Accordingly, it may be necessary to have high sensitivity to allow for measurement of small values of capacitance. One high sensitivity sensor is the charge transfer sensor circuit described above. Other high sensitivity sensors are provided by such devices as the PTL 110 capacitance transducer from Process Tomography Limited of Cheshire, United Kingdom. The PTL 110 measures small values of capacitance (up to 10 picoFarads) with a resolution of 1 femtoFarad. A 1616 Precision Capacitance Bridge from IET Labs, Inc. of Westbury, N.Y., allows for measurement of capacitances in the range from 10-7 pF to 10 µF. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCs) can easily obtain resolutions to 0.01 pF.

In one embodiment, sensor S2 is a piezoelectric microbalance (e.g., a quartz crystal microbalance) sensor that supports a chemical that interacts with the decontaminant present in fluid 38. As the component of the fluid to be detected interacts with the chemical supported by sensor S2, the frequency of sensor S2 changes accordingly. The change in frequency of sensor S2 is compared to data or graphs stored in processing system 34 that correlate the change in frequency of sensor 34 with concentrations of the decontaminant present in fluid 38. Sensor S2 is more fully described in U.S. patent application entitled, Sensor for Determining Concentration of Fluid Sterilant (Ser. No. 10/663,593), which is fully incorporated herein by reference.

Figure 6:
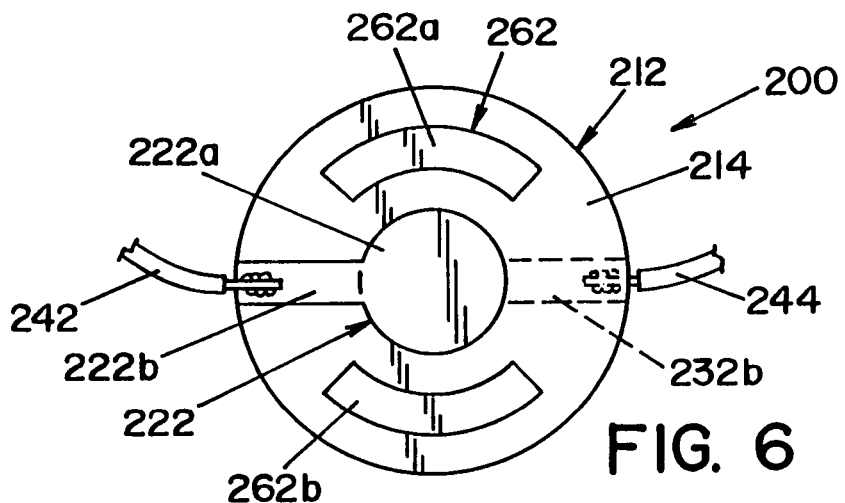
FIG. 6 is a top, plan view of an exemplary piezoelectric microbalance sensor for determining the concentration of a chemical component, according to a preferred embodiment.
Figure 7:
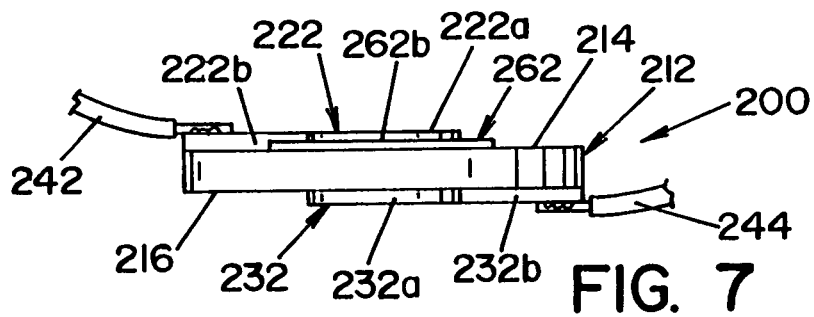
FIG. 7 is a side, elevation view of the piezoelectric microbalance sensor shown in FIG. 6.
Figure 8:
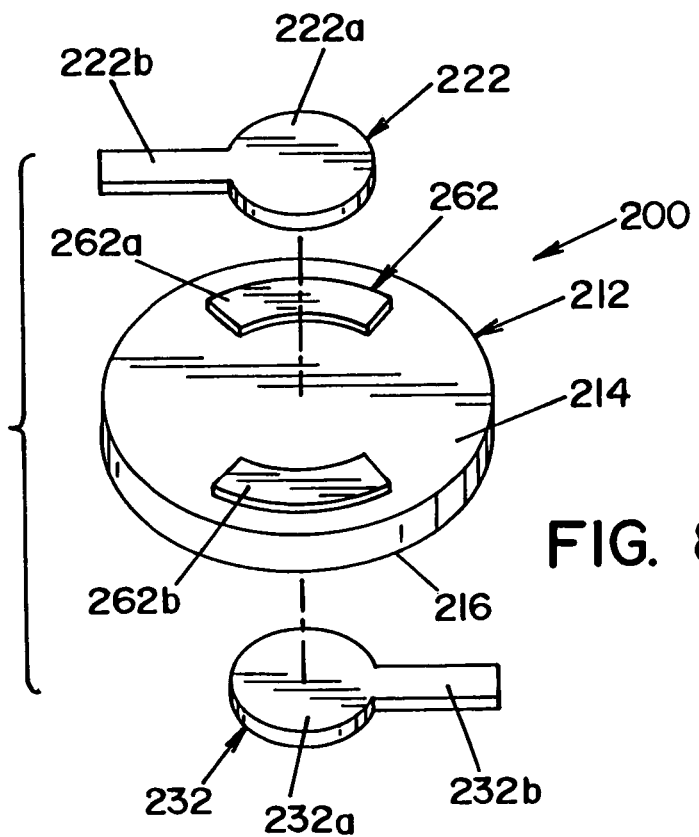
FIG. 8 is an exploded view of the piezoelectric microbalance sensor shown in FIG. 6.

Referring now to FIGS. 6-8, there is shown a block diagram of an exemplary sensor 200, according to a first embodiment, that may be used as sensor S2. Sensor 200 includes a sensing element 212 having a layer or coating 262 of a material that interacts with, or is reactive with, a chemical component of fluid 38, such that mechanical motion or movement of sensor 200 is converted into an electrical signal and transmitted to processing system 34.

Element 212 may be a moving or suspended component, but in a preferred embodiment, element 212 is a piezoelectric device, and more preferably, is a quartz crystal. Other piezoelectric materials, such as by way of example and not limitation, Rochelle salt, barium titanate, tourmaline, polyvinylidene fluoride and crystals that lack a center of symmetry are also contemplated. In the embodiment shown, element 212 is a flat, circular quartz disk having a first planar, major surface 214 and a second planar, major surface 216. An electrode 222 is disposed on the first major surface 214 and an electrode 232 is disposed optionally on the second major surface 216.

Electrode 222 includes a main body portion 222a that is centrally disposed on first major surface 214 and a leg portion 222b that extends in a first direction to the edge of element 212. Similarly, electrode 232 includes a main body portion 232a that is centrally disposed on second major planar surface 216, and a leg portion 232b that extends in a direction opposite to the first direction of leg portion 222b, wherein leg portion 232b extends to the edge of element 212. Main body portions 222a, 232a of electrodes 222, 232 are disposed respectively on first and second major surfaces 214, 216 to be aligned with each other on opposite sides of element 212. Leg portions 222b, 232b extend in opposite directions from central body portions 222a, 232a, as best seen in the drawings. Electrodes 222, 232 are deposited onto first and second planar surfaces 214, 216. Electrodes 222, 232 may be formed of any electrically conductive material, but are preferably formed of copper, silver or gold. Electrical leads 242, 244 are attached to leg portions 222b, 232b of electrodes 222, 232. Leads 242, 244 are soldered, brazed or welded to electrodes 222, 232 to be in electrical contact therewith.

At least one of the two major surfaces 214, 216 of element 212 is coated with a layer 262 of a material that interacts, or is reactive with, a chemical component of fluid 38. In the embodiment shown, layer 262 is on major surface 214. In the embodiment shown, layer 262 is defined by two arcuate or crescent-shaped layer areas 262a, 262b of material applied to first major surface 214 of element 212. Arcuate layer areas 262a, 262b are disposed on first major surface 214 such that electrode 222 is disposed therebetween. The material forming layer areas 262a, 262b are preferably fixedly attached to surface 214 of element 212. The mass of the material on element 212 is dependent upon the desired performance characteristics of sensor 200. As indicated above, the material forming layer areas 262a, 262b is preferably one that interacts or reacts with a chemical component of fluid 38.

Where the chemical component to be detected by vapor concentration sensor 200 is vaporized hydrogen peroxide, and the material that forms layer areas 262a, 262b on first major surface 214 of vapor concentration sensor 200 is a metal oxide, namely, lead dioxide ($PbO_2$). It is believed that other metal oxides having various states, such as silver (II) oxide (AgO) or manganese (IV) oxide ($MnO_2$), may be used. It is also contemplated that metal oxides having mixed valency states, such as by way of example and not limitation, a metal oxide having a mixture of single and divalent oxide states may be used.

In the illustrated embodiment, sensor 200 is disposed within interior region 16 of chamber 2 and is connected to processing system 34 as shown in FIG. 1, to provide electrical signals thereto.

Processing system 34 includes an oscillating circuit (not shown) that is connected to sensor 200 to convert movement of sensor 200 into electrical signals, as is conventionally known. As indicated above, processing system 34 also includes a data storage device for storing data indicative of the electrical responses of sensor 200 to predetermined concentrations of a chemical component to be sensed. In the embodiment heretofore described, where sensor 200 is a quartz crystal and layer areas 262a, 262b are lead dioxide, the data relating to sensor 200 that is stored within processing system 34 is empirical data accumulated under controlled, laboratory conditions.

The empirical data relating to sensor 200 that is stored in the data storage device of processing system 34 may be acquired as follows. The natural frequency of a quartz crystal (without a coating thereon) is measured. The lead dioxide is applied to the quartz crystal and the mass of the coating is determined using the Sauerbre equation. The quartz crystal is then exposed to various, controlled concentrations of the chemical component (e.g., vaporized hydrogen peroxide). A graph of the change in frequency per unit mass of coating (or, using the Sauerbre equation, the change in weight per unit mass of coating) versus concentration of chemical component is produced and stored in the data storage device of processing system 34. Alternatively, the data could be stored not as a graph but rather in look-up data tables. As will be appreciated, if a coating of uniform thickness is applied to a crystal, the change in frequency or weight could be normalized on a per unit surface area basis.

As suggested, in one embodiment, the change in frequency or weight is divided by the mass of the coating applied to the quartz crystal so that regardless of the mass of coatings applied to other crystals, the change in frequency will be normalized to a unit mass of the coating. Data taken with other quartz crystals that may have coatings of different amounts of mass than the laboratory crystal can still be compared to the stored data obtained from the laboratory crystal as both sets of data will be normalized to a change in frequency or weight per unit mass of the coating. It will be appreciated that with modern deposition means, it may not be necessary to normalize the data as coatings with little physical variation can be deposited from one crystal to the next.

In another embodiment, a quartz crystal is coated with lead oxide and is then exposed to known concentrations of a chemical component (e.g., vaporized hydrogen peroxide) so as to develop a set of data, or a curve, of equilibrium frequency reduction values as a function of concentration of the chemical component for the quartz crystal. The coated quartz crystal is then installed in system 10. The associated set of data, or curve, is programmed or stored in the data storage device of processing system 34. Thus, the data stored in processing system 34 matches the crystal sensor within sensor 200, thereby providing a standardized system. In this manner, sensor 200 has a coated quartz crystal sensor with an associated standardized data set stored within the data storage device of processing system 34, as the stored data set was produced by exposing that specific quartz crystal to known concentrations of the chemical component.

Sensor 200 operates based upon the concept that the frequency of a piezoelectric device will change in relation to a change in mass of a layer on the device, as a result of exposure to vaporized hydrogen peroxide.

Specifically, the frequency of a piezoelectric device is related to the mass change, as determined by the Sauerbre equation:

$$\Delta f = -(C_f)(\Delta m)$$

$$\Delta f = -(f_o^2/N\rho)\Delta m$$

where: $\Delta f$ is the frequency change, $\Delta m$ is the mass change per unit area on the surface of the piezoelectric device, $C_f$ is a sensitivity constant, $f_o$ is the operating frequency of the piezoelectric device prior to the mass change, N is the frequency constant for the piezoelectric device, and $\rho$ is the density of the piezoelectric device.

In one embodiment, sensor S1 (a capacitor), with processing system 34, detects and measures the concentration of a chemical component, in this case, a decontaminant, present in fluid 38 by sensing changes in the electrical properties of fluid 38. Sensor S2, with processing system 34, detects and measures the concentration of the same chemical component, in this case, a decontaminant, of fluid 38 by sensing changes in the frequency of a piezoelectric material, such as quartz, that supports a chemical that interacts with the decontaminant. Sensor S2 either directly or indirectly senses the mass of the decontaminant in fluid 38 as the decontaminant interacts with the decontaminant-specific chemical located on the quartz crystal. Thus, each of sensor S1 and sensor S2, with processing system 34, measures the concentration of a chemical component, in this case a decontaminant, present in fluid 38 by sensing a different physico-chemical, i.e., physical and/or chemical, property of the chemical component or, in this embodiment, the decontaminant, present in fluid 38. The physico-chemical property may include an electromagnetic property, i.e., an interaction with electromagnetic radiation including, but not limited to, interaction with infrared radiation. Sensor system 20, with processing system 34, then monitors and controls the concentration of the chemical component or decontaminant present in fluid 38 so as to maintain the concentration of the chemical component or decontaminant in fluid 38 at a suitable, desired or required level.

FIG. 2 shows a flow diagram 40 illustrating the operation of sterilization system 10 and sensor system 20. After fluid 38 is introduced to chamber 2 through input line 6, in step 42, processing system 34 senses a change in an electrical signal of sensor S1. In step 44, processing system 34 senses a change in an electrical signal of sensor S2. In steps 46 and 48, the electrical signal of each sensor S1, S2 is referenced to stored data or a stored graph, and the concentration of the chemical component (decontaminant) is determined. Referring to steps 50 and 52, if the concentration of the chemical component as determined using one sensor falls within a set percentage of the concentration as determined by using the other sensor, then processing system 34 and sensor system 20 continue to monitor and control the concentration of the chemical component in fluid 38 (step 54). Alternatively, if the concentration of the chemical component, as determined by using one sensor, falls outside of a set percentage of the concentration as determined by using the other sensor, then processing system 34 communicates this information to control unit 36, and control unit 36 is programmed to abort the chemical process or sterilization cycle or responds in a pre-programmed manner (step 56), such as, by way of example and not limitation, sounding an alarm, suspending the chemical process or sterilization cycle or sending an electronic signal to a remote computer (not shown), thus alerting a remote operator or controller that the sensors S1, S2 are not measuring the same concentration of the chemical component (decontaminant) in fluid 38. In this case, one, or both, of sensors S1, S2 is defective, is not operating properly and must be serviced. Since both sensors S1 and S2 are inexpensive, one may simply replace both sensors S1 and S2 at the same time thus insuring that sensor system 20 is fully operational. Upon installing a new sensor system 20, one may have to load into the data storage device of processing system 34 new correlating data obtained for new sensor system 20. Optionally, sensor S1 or sensor S2 may be individually replaced. Thus, inasmuch as each sensor S1, S2 is sensing a different physico-chemical property of the chemical component (decontaminant), sensor system 20, with processing system 34, operates as a "self-policing" system.

In one embodiment, the stored data or graphs referenced hereinabove constitute data obtained from controlled, laboratory measurements wherein various concentrations of the chemical component (decontaminant) are created under controlled conditions. Thus, once a given concentration of the chemical component (decontaminant) in a fluid is established, i.e., as measured by sophisticated analytical instruments, a datum point of a particular physico-chemical property of the chemical component (decontaminant) or fluid is taken using each sensor S1, S2. The process is continued. Namely, further concentrations of the chemical component (decontaminant) in fluid 38 are established by the analytical laboratory equipment and data points are taken using each sensor S1, S2, at each concentration. The data are stored in the data storage device of processing system 34 of sterilization system 10 To obtain a fully calibrated system, the sensors used in the laboratory to generate the data and the data generated are used in the same sterilization system 10.

Generally, sensor system 20, with processing system 34, is designed to be a self-policing system. Namely, if the concentration of a chemical component as measured using one sensor falls within a set percentage (to account for experimental error) of the concentration as measured using the other sensor, then sensor system 20, with processing system 34, provides evidence that supports the measured and determined concentration of the chemical component (decontaminant) of fluid 38. If both sensors S1, S2, with processing system 34, provide a consistent value for the concentration of the chemical component, it is likely that the measured concentration is proper. This is especially persuasive given that each sensor S1, S2 is used to measure a different physico-chemical property of the chemical component or decontaminant in fluid 38.

If the measured concentration is below or above a set range, then processing system 34 sends an electrical signal to control unit 36. Control unit 36 then takes corrective action to place the concentration of the chemical component (decontaminant) in accordance with a pre-set specification.

In the event the process is a decontamination process, sensor system 20 and processing system 34 of the present invention provide an added benefit. Namely, sensor system 20 and processing system 34 are capable of recording, i.e., either electronically or in visual form (e.g., using an output device, such as a monitor or printer), the history of the concentration of the decontaminant throughout the course of a decontamination cycle. Coupling the self-policing capabilities of sensor system 20, with processing system 34, with the capability of processing system 34 to record the concentrations of the decontaminant throughout the course of a decontamination cycle provides persuasive evidence that a decontamination cycle is effective.

Other physico-chemical properties of chemical component of fluid 38, i.e., in addition to electrical properties and gravimetric properties, that either sensor S1 or S2 with processing system 34 can measure include, but are not limited to: magnetic properties, thermal properties, photo properties, such as, by way of example and not limitation, interactions with electromagnetic waves, including, by way of example and not limitation, absorption of electromagnetic radiation such as, by way of example and not limitation, infrared, mid-infrared, near infrared, ultraviolet or visible electromagnetic radiation, physical properties, chemical properties including, by way of example and not limitation, chemical reactions with the sensor that result in a change in a physical and/or chemical property of the sensor itself (see U.S. patent application entitled, Sensor for Detecting a Chemical Component Concentration Using an Electroactive Material (Ser. No. 10/608,276), incorporated herein by reference, as an example), chemisorption, physisorption, adsorption and absorption.

By way of example and not limitation, the following decontaminants may be detected, measured and controlled by the aforementioned system: detergent, soap, steam, water vapor, vaporized hydrogen peroxide, ethylene oxide, ozone, ammonia, halogen containing compounds such as chlorine or bromine containing compounds, liquid hydrogen peroxide, peracidic acid, peracids, bleach, alcohol (e.g., a tertiary alcohol), iodophors, quaternary ammonium chlorides (Quats), acid sanitizers, aldehydes (formaldehyde and glutaraldehyde), phenolics, chlorine dioxide and oxidative chemicals.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A method of monitoring operational status of sensing devices for determining a concentration of a chemical component in a fluid, comprising the steps of:
   sensing a first physico-chemical property of the chemical component by measuring a first electrical signal produced by a first sensor;
   determining a first concentration of the chemical component by referencing the first electrical signal to a first set of stored data;
   sensing a second physico-chemical property of the chemical component by measuring a second electrical signal produced by a second sensor, wherein the first physico-chemical property is different from the second physico-chemical property;
   determining a second concentration of the chemical component by referencing the second electrical signal to a second set of stored data;
   comparing the first concentration to the second concentration to determine whether the first concentration falls within a pre-set percentage of the second concentration; and
   determining that at least one of said first and second sensors is defective if the first concentration falls outside the pre-set percentage of the second concentration.

2. The method of claim 1, wherein the chemical component is a decontaminant.

3. The method of claim 1, wherein the fluid is a liquid.

4. The method of claim 3, wherein the liquid is water.

5. The method of claim 1, wherein the fluid is a gas.

6. The method of claim 5, wherein the gas is air.

7. The method of claim 1, wherein the first sensor comprises a capacitor and the second sensor comprises a piezoelectric material.

8. The method of claim 7, wherein the piezoelectric material is a quartz crystal that supports a chemical that interacts with the decontaminant.

9. The method of claim 1, wherein the decontaminant is selected from the group consisting of: detergent, soap, steam, water vapor, vaporized hydrogen peroxide, ethylene oxide, ozone, ammonia, halogen containing compounds, liquid hydrogen peroxide, peracidic acid, per acids, bleach, alcohol, iodophors, quaternary ammonium chlorides, acid sanitizers, aldehydes, phenolics, chlorine dioxide and combinations thereof.

10. The method of claim 1, wherein the decontaminant is vaporized hydrogen peroxide.

11. The method of claim 1, wherein the decontaminant is liquid hydrogen peroxide.

12. The method of claim 1, wherein the decontaminant is an oxidative chemical.

13. The method of claim 1, wherein the decontaminant is a detergent.

14. The method of claim 1, wherein at least one of said first physico-chemical property and said second physico-chemical property is an electromagnetic property of the chemical component.

15. The method of claim 14, wherein said electromagnetic property of the chemical component is in the infrared.

* * * * *